United States Patent [19]

Sprecker

[11] Patent Number: 4,652,400
[45] Date of Patent: Mar. 24, 1987

[54] 5-NITRO-1,1,2,3,3-PENTAMETHYL INDANE DERIVATIVES AND PERFUMERY USES THEREOF

[75] Inventor: Mark A. Sprecker, Sea Bright, N.J.

[73] Assignee: International Flavors & Fragrances Inc., New York, N.Y.

[21] Appl. No.: 850,584

[22] Filed: Apr. 11, 1986

[51] Int. Cl.$^4$ ............................. A61K 7/46; C11B 9/00
[52] U.S. Cl. .................................. 252/522 R; 568/939; 71/124
[58] Field of Search ..................... 252/522 R; 568/939; 71/124, 125

[56] References Cited

U.S. PATENT DOCUMENTS

| | | | |
|---|---|---|---|
| 2,768,982 | 1/1956 | Schlatter | 260/668 |
| 3,283,016 | 11/1966 | Woods et al. | 260/645 |
| 3,393,995 | 7/1968 | Evans et al. | 71/125 |
| 3,442,640 | 5/1969 | Woods et al. | 71/124 |

OTHER PUBLICATIONS

Bedoukian, "Perfumery and Flavoring Synthesis" 2nd ed., Published 1967, see pp. 269–280.
Arctander, "Perfume and Flavor Chem. (Aroma Chem.)", vol. II, Pub. by Author 1969, Monograph 2275, use of 1,1,3,3,5–Pentamethyl-4,6–Dinitroindane.

Primary Examiner—Werren B. Lone
Attorney, Agent, or Firm—Arthur L. Liberman

[57] ABSTRACT

Described are 5-nitro-1,1,2,3,3-pentamethyl indane derivatives defined according to the generic structure:

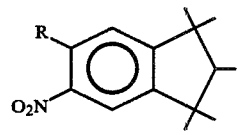

wherein R represents hydrogen or methyl and uses thereof in augmenting or enhancing the aroma of consumable materials selected from the group consisting of perfume compositions, colognes and perfumed articles.

6 Claims, 6 Drawing Figures

GLC PROFILE FOR EXAMPLE I.

GLC PROFILE FOR EXAMPLE II.

GLC PROFILE FOR EXAMPLE II.

GLC PROFILE FOR EXAMPLE I.

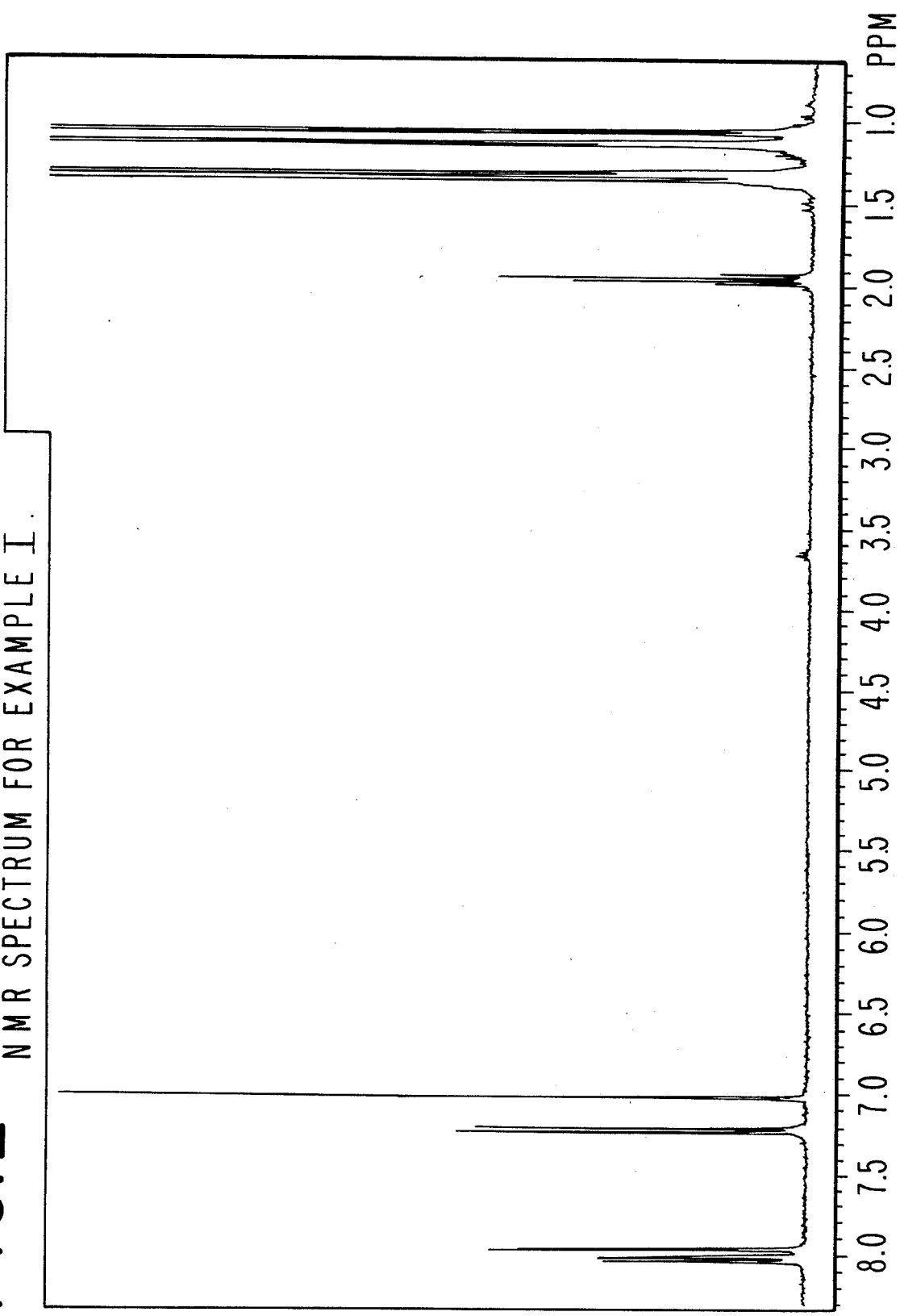
FIG. 2 NMR SPECTRUM FOR EXAMPLE I.

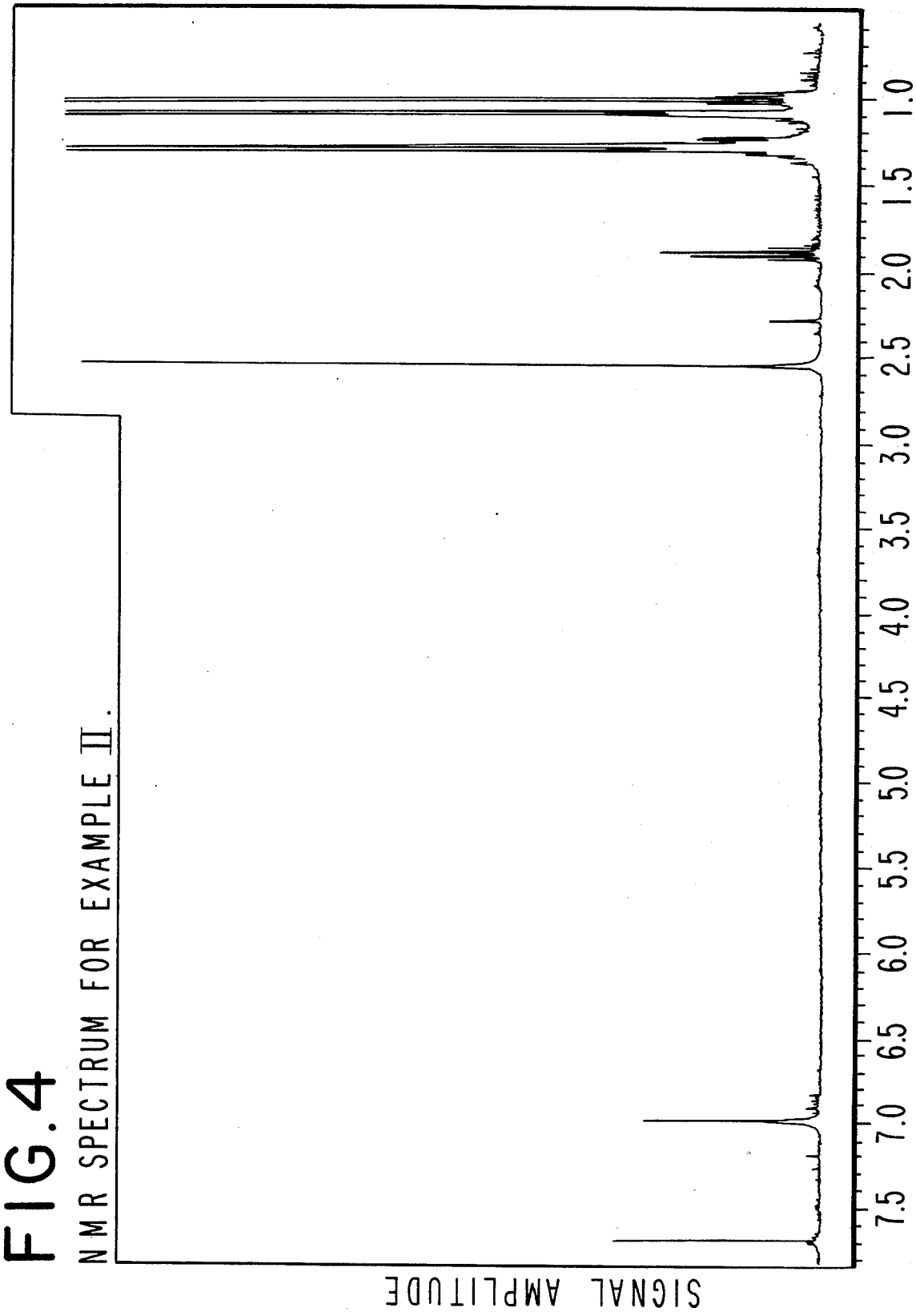
FIG. 4 NMR SPECTRUM FOR EXAMPLE II.

5-NITRO-1,1,2,3,3-PENTAMETHYL INDANE DERIVATIVES AND PERFUMERY USES THEREOF

BACKGROUND OF THE INVENTION

The present invention relates to 5-nitro-1,1,2,3,3-pentamethyl indane derivatives having the structure:

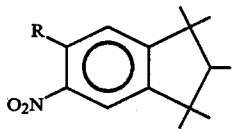

wherein R represents hydrogen or methyl and uses thereof in augmenting or enhancing the aroma of perfume compositions, perfumed articles and colognes.

There has been considerable work performed relating to substances which can be used to impart (modify, augment or enhance) fragrances to (or in) various consumable materials. Such substances are used to diminish the use of expensive natural materials some of which may be in short supply and to provide more uniform properties in the finished product.

Long-lasting, substantive, and intense sweet, musky aroma nuances are particularly desirable in several types of perfume compositions, perfumed articles and colognes.

Bicyclic compounds having nitro substituents bonded thereto are well known for use as musk nuances in the perfumery industry.

Thus, U.S. Pat. No. 3,283,016 issued on November 1, 1966 discloses compounds having the generic structure:

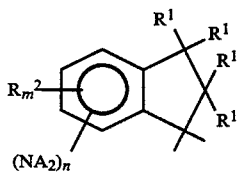

wherein A can represent oxygen, and R can represent alkyl, and m can represent 1, and $R_1$ can represent methyl, and n can represent 1 as being useful in perfumery; but the genus set forth therein does not include the genus defined according to the structure:

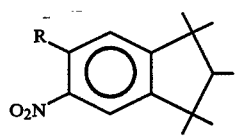

and the genus set forth in said U.S. Pat. No. 3,283,016 discloses the compounds having the structures:

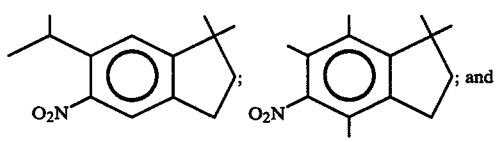

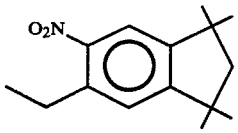

primarily for use as herbicides and incidentally, indicates "some of the compounds have properties making them suitable for use in perfumery, e.g., as musk odorants".

Arctander "Perfume and Flavor Chemicals (Aroma Chemicals)", Volume 2, at Monograph 2275 discloses "Moskene" a tradename of a chemical marketed by The Givaudan Corporation having the structure:

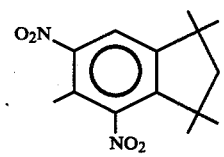

prepared according to the reaction:

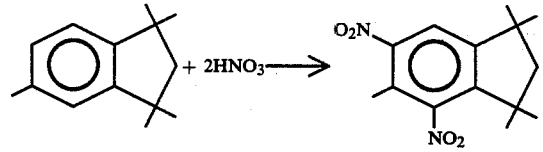

by nitrating the compound having the structure:

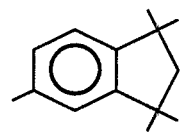

and discloses that this compound has a musky, sweet odor of the type resembling musk ketone and musk ambrette, yet more creamy-floral, sweeter and more tenacious.

Wood, et al, U.S. Pat. No. 3,442,640 issued on May 6, 1969 discloses for use as herbicides the dinitro derivatives defined according to the structure:

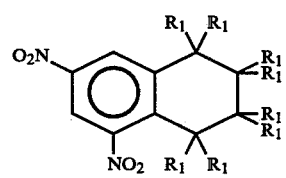

wherein $R_1$ represents $C_1$-$C_5$ alkyl or hydrogen but does not infer that these compounds are useful in perfumery. Ying-Hung So, U.S. Pat. No. 4,570,011 discloses compounds having the generic structure:

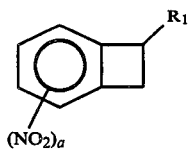

wherein a represents an interger of from 1 up to 4 and $R_1$ is hydrogen or $C_1$-$C_{20}$ for use as intermediates for preparing polymers.

U.S. Pat. No. 2,768,982 issued on Oct. 30, 1956, at column 2, lines 10–20 discloses the compound having the structure:

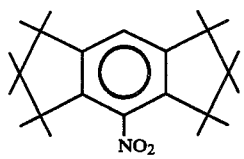

as useful in perfumery but does not disclose any details for its use.

Nothing in the prior art discloses the long-lasting substantive and intense sweet, musky aroma of the compounds defined according to the generic structure:

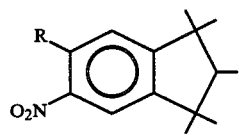

wherein R is hydrogen or methyl and the properties of such genus defined according to the structure:

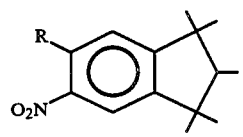

are unexpected, unobvious and advantageous in the field of perfumery.

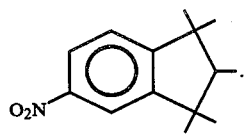

FIG. 2 is the NMR spectrum for the compound having the structure:

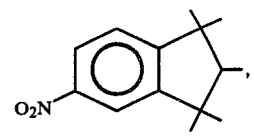

produced according to Example I.

Figure 3:
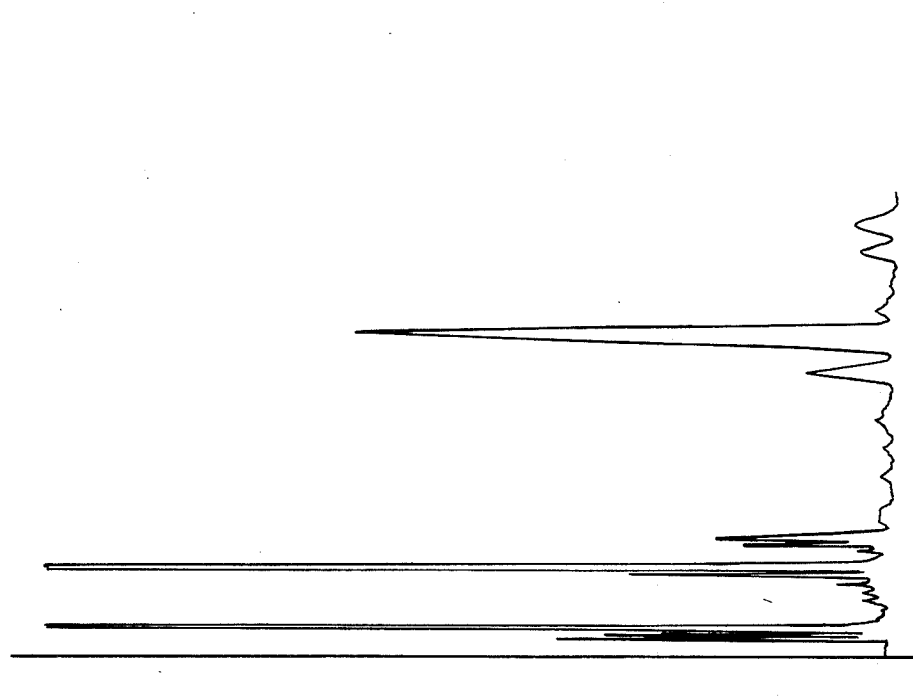

FIG. 3 is the GLC profile for the crude reaction product of Example II containing the compound having the structure:

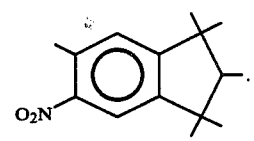

FIG. 4 is the NMR spectrum for the compound having the structure:

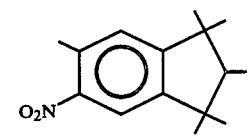

produced according to Example II.

Figure 5:
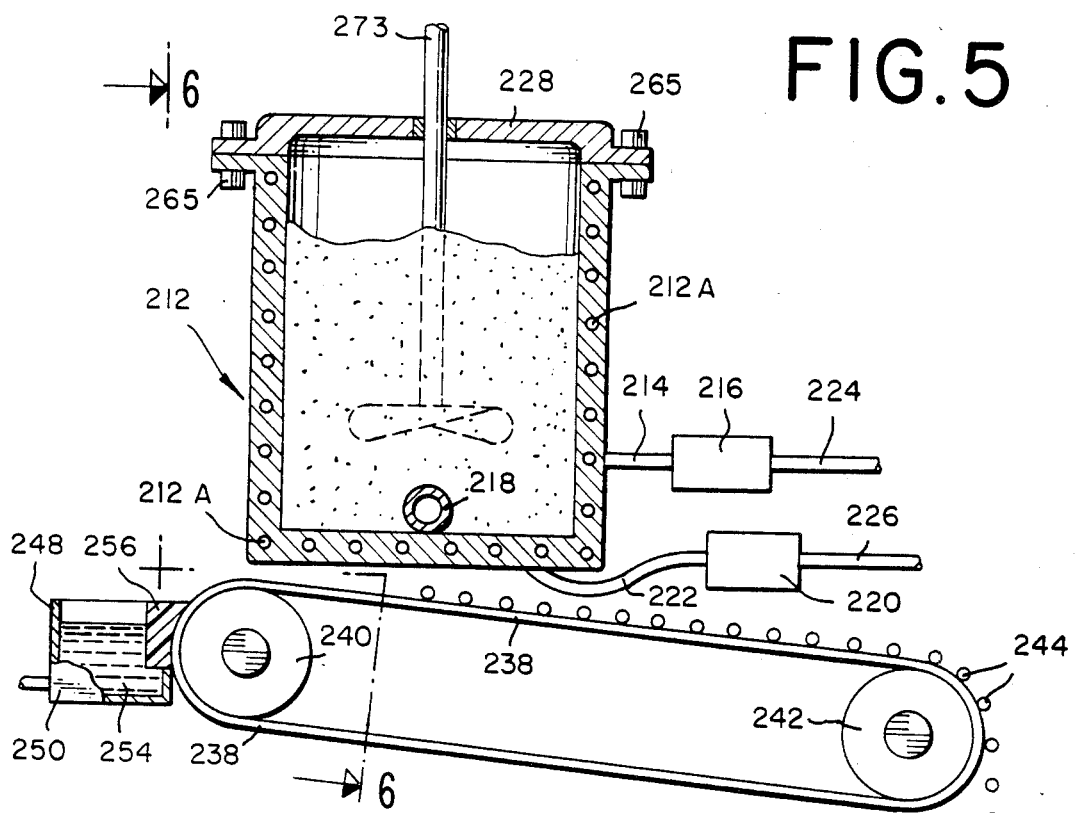

FIG. 5 represents a cut-away side elevation view of apparatus used in forming perfume polymers which contain embedded therein the 5-nitro-1,1,2,3,3-pentamethyl indane derivatives of my invention.

Figure 6:
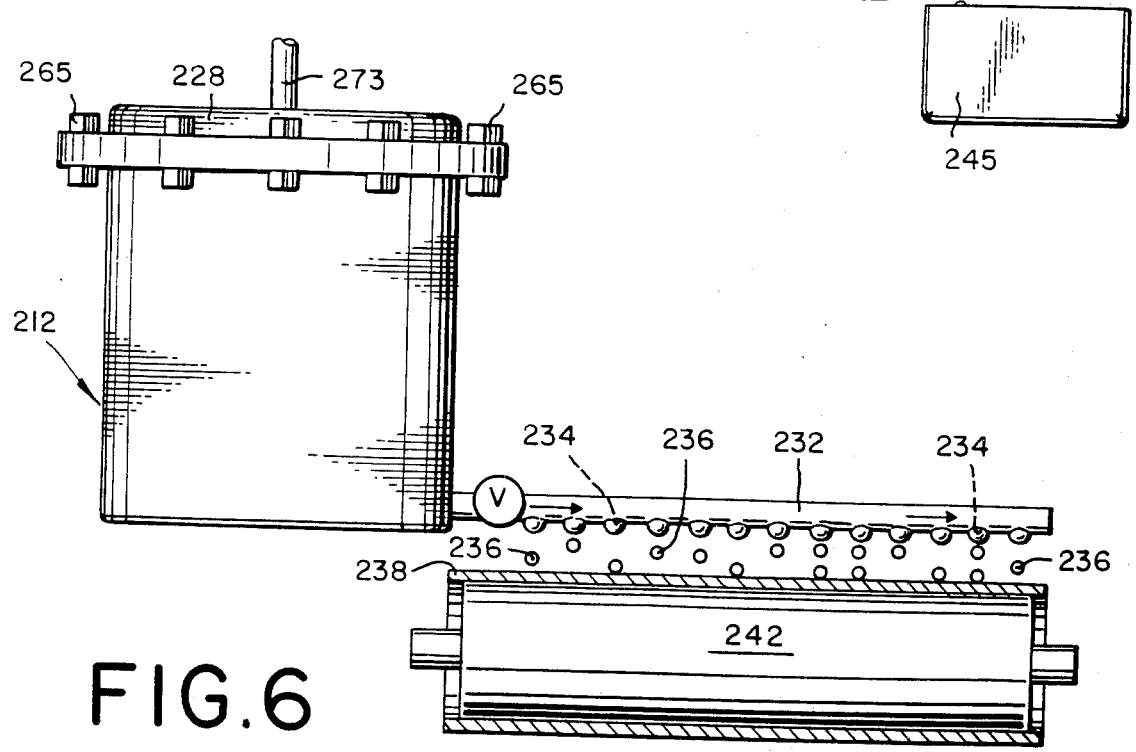

FIG. 6 is a front view of the apparatus of FIG. 5 looking in the direction of the arrows.

DETAILED DESCRIPTION OF THE DRAWINGS

Referring to FIGS. 5 and 6, there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfume. The process comprises heating the polymer or mixture of polymers to the melting point of said polymer or mixture of polymers, e.g., 250° C. in the case of low density polyethylene. The lower-most portion of the container is maintained at a slightly lower temperature and the material in the container is taken off at such location for delivery through the conduit. Thus, referring to FIGS. 5 and 6, in particular, the apparatus used in producing such elements comprises a device for forming the polymer containing perfume, e.g., polyethylene or polyethylenepolyvinyl acetate or mixtures of same or polypropylene, which comprises a vat or container 212 into which the polymer taken alone or in admixture with other copolymers and the perfuming substance which contains one or more of the 5-nitro-1,1,2,3,3-pentamethyl indane derivatives of my invention or mixtures of the 5-nitro-1,1,2,3,3-pentamethyl indane derivatives of my invention and other compatible perfumes, is placed. The container is closed by means of an air-tight lid 228 and clamped to the container by bolts 265. A stirrer 273 traverses the lid or cover 228 in an air-tight manner and is rotatable in a suitable manner. A surrounding cylinder 212A having heating coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 saybolt seconds. The heater 218 is operated to maintain the upper portion of the container 212 within the temperature range of, for example, 220°–270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°–270° C.

Thus, the polymer or mixture of polymers added to the container 212 is heated from 10–12 hours, whereafter the perfume composition or perfume material which contains one or more of the 5-nitro-1,1,2,3,3-pentamethyl indane derivatives of my invention is quickly added to the melt. Generally, about 10–45 percent by weight of the resulting mixture of the perfumery substance is added to the polymer.

After the perfume material is added to the container 212, the mixture is stirred for a few minutes, for example, 5–15 minutes and maintained within the temperature ranges indicated previously by the heating coils 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with one or more of the 5-nitro-1,1,2,3,3-pentamethyl indane derivatives of my invention or mixture of perfume substances and one or more of the 5-nitro-1,1,2,3,3-pentamethyl indane derivatives of my invention, will continuously drop through the orifices 234 downwardly from the conduit 232. During this time, the temperature of the polymer intimately admixed with the perfumery substance in the container 212 is accurately controlled so that a temperature in the range of from about 240°–250° C., for example, (in the case of the low density polyethylene) will exist in the conduit 232. The regulation of the temperature through the controls 216 and 220 is essential in order to insure temperature balance to provide for the continuous dripping or dropping of molten polymer intimately admixed with the perfume substance which is all of or which contains one or more of the 5-nitro-1,1,2,3,3-pentamethyl indane derivatives of my invention, through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into container 250 which is advantageously filled with water or some other suitable cooling liquid to insure the rapid cooling of each of the pellets 244. The pellets 244 are then collected from the container 250 and utilized for the formation of other functional products, e.g., garbage bags and the like.

THE INVENTION

The present invention provides 5-nitro-1,1,2,3,3-pentamethyl indane derivatives defined according to the generic structure:

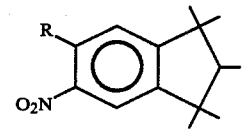

wherein R represents hydrogen or methyl.

The 5-nitro-1,1,2,3,3-pentamethyl indane derivatives of my invention produced according to the process of my invention are capable of augmenting or enhancing sweet, musky aroma characteristics in perfume compositions and perfumed articles. Unexpectedly, and advantageously, the 5-nitro-1,1,2,3,3-pentamethyl indane derivatives of my invention have long-lasting, highly intense, highly substantive, sweet, musk nuances. Accordingly, a need in the field of perfumery has been fulfilled by the provision of the 5-nitro-1,1,2,3,3-pentamethyl indane derivatives of my invention.

The 5-nitro-1,1,2,3,3-pentamethyl indane derivatives of my invention are produced using as a starting material a pentamethyl indane derivative defined according to the structure:

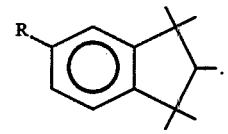

The compound having the structure:

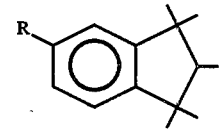

is first admixed with at least an equal volume of a weak acid such as acetic acid. The resulting mixture is then admixed with fuming nitric acid and a small amount of sulfuric acid at a temperature in the range of from about 20° C. up to about 30° C. for a period of time of from about two hours up to about ten hours according to the reaction:

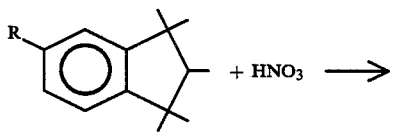

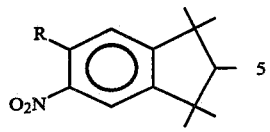

wherein R represents hydrogen or methyl. The weight ratio of sulfuric acid to nitric acid is in the range of from about 1:8 up to about 1:2 with a preferred weight ratio of about 1:4. The weight ratio of weak acid, e.g., acetic acid to indane hydrocarbon having the structure:

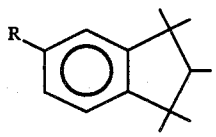

is from about 3:1 down to about 1:1 with a preferred weight ratio of about 2:1. The weight ratio of nitric acid to hydrocarbon having the structure:

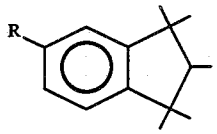

may vary from about 2:1 up to about 1:2 with a weight ratio of about 4:5 being preferred.

At the end of the reaction, the reaction mass is quenched with water and the resulting products defined according to the structure:

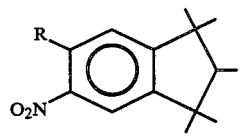

crystallize out as substantially pure compound having the structure:

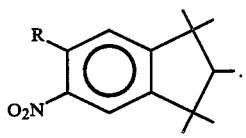

The genus having the structure:

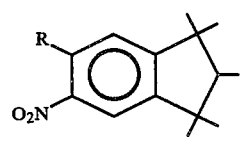

contains two compounds, to wit: the compound having the structure:

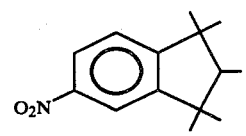

and the compound having the structure:

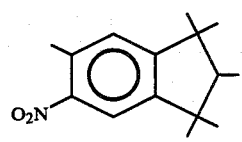

The compound having the structure:

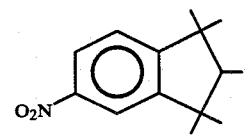

is prepared according to the reaction:

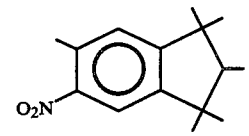

and the compound having the structure:

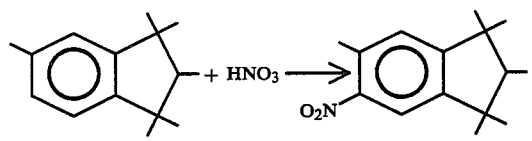

is prepared according to the reaction:

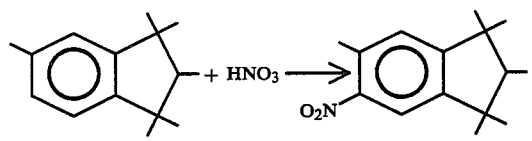

by treating, respectively, the indane having the structure:

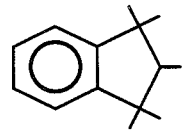

or the indane having the structure:

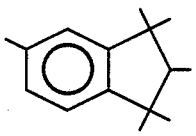

with nitric acid in the presence of sulfuric acid. One or more of the 5-nitro-1,1,2,3,3-pentamethyl indane derivatives of my invention and one or more auxiliary perfume ingredients, including, for example, alcohols, aldehydes, ketones, terpenic hydrocarbons, nitriles, esters, lactones, nitro derivatives other than the 5-nitro-1,1,2,3,3-pentamethyl indane derivatives of my invention, natural essential oils and synthetic essential oils may be admixed so that the combined odors of the individual components produce a pleasant and desired fragrance, particularly, and preferably, in musk fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling, fresh-smelling materials.

In perfume compositions, it is the individual components which contribute to their particular olfactory characteristics, however, the overall sensory effect of the perfume composition will be at least the sum total of the effects of each of the ingredients. Thus, one of the 5-nitro-1,1,2,3,3-pentamethyl indane derivatives prepared in accordance with the processes of my invention can be used to alter, modify, or enhance the aroma characteristics of a perfume composition, for example, by utilizing or modifying the olfactory reaction contributed by another ingredient in the composition.

The amount of one of the 5-nitro-1,1,2,3,3-pentamethyl indane derivatives prepared in accordance with the process of my invention which will be effective in perfume compositions as well as in perfumed articles (e.g., anionic, cationic, nonionic or zwitterionic detergents, soaps and fabric softener compositions and articles) and colognes depends upon many factors including the other ingredients, their amounts, and the effects which are desired. It has been found that perfume compositions containing as little as 0.01% of one or more of the 5-nitro-1,1,2,3,3-pentamethyl indane derivatives prepared in accordance with the process of my invention and less than 50% of one or more of the 5-nitro-1,1,2,3,3-pentamethyl indane derivatives prepared in accordance with the process of my invention or even less (e.g., 0.005%) can be used to impart a sweet, musky, long-lasting, intense aroma to soaps, cosmetics, anionic, cationic, nonionic or zwitterionic detergents, fabric softener compositions, fabric softener articles, perfumed polymers or other perfumed articles. The amount employed can range up to 70% of the fragrance components and will depend on considerations of cost, nature of the end product, the effect desired on the finished product and the particular fragrance sought.

One or more of the 5-nitro-1,1,2,3,3-pentamethyl indane derivatives of my invention are useful (taken alone or taken further together with other ingredients in perfume compositions) as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders, perfumed polymers and the like. When used as (an) olfactory component(s) as little as 0.2% of one or more of the 5-nitro-1,1,2,3,3-pentamethyl indane derivatives of my invention will suffice to impart a long-lasting intense, substantive sweet, musky aroma to musk formulations. Generally, no more than 6% of one or more of the 5-nitro-1,1,2,3,3-penta-methyl indane derivatives of my invention based on the ultimate end product are required in the perfumed article composition. Accordingly, the range of one or more of the 5-nitro-1,1,2,3,3-pentamethyl indane derivatives of my invention in a perfumed article may vary from about 0.2% up to about 6% by weight of the ultimate perfumed article.

In addition, the perfume composition or fragrance compositions of my invention can contain a vehicle or carrier for the 5-nitro-1,1,2,3,3-pentamethyl indane derivatives of my invention. The vehicle can be a liquid, such as non-toxic alcohol, e.g., ethyl alcohol, a non-toxic glycol, e.g., propylene glycol or the like. The carrier can also be an absorbent solid such as a gum (e.g., gum arabic, xanthan or guar gum) or components for encapsulating the composition (such as gelatin as by coacervation or such as a urea-formaldehyde prepolymer when forming a urea-formaldehyde polymer wall around a liquid perfume center).

It will thus be apparent that the 5-nitro-1,1,2,3,3-pentamethyl indane derivatives of my invention can be utilized to alter, modify or enhance sensory properties, particularly organoleptic properties such as fragrance of a wide variety of consumable materials.

The following Examples I and II illustrate methods of my invention used to prepare the 5-nitro-1,1,2,3,3-pentamethyl indane derivatives of my invention. Examples III, et seq. illustrate the organoleptic utilities of the 5-nitro-1,1,2,3,3-pentamethyl indane derivatives of my invention.

All parts and percentages given herein are by weight unless otherwise specified.

EXAMPLE I

PREPARATION OF 5-NITRO-1,1,2,3,3-PENTAMETHYL INDANE

Reaction:

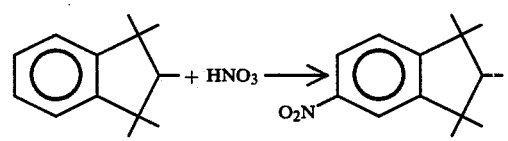

Into a 500 ml reaction vessel equipped with stirrer, thermometer, reflux condenser, addition funnel and cooling bath is placed 50 grams of 1,1,2,3,3-pentamethyl indane having the structure:

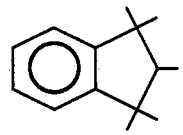

in admixture with 100 grams of acetic acid. While maintaining the reaction mass at 25° C., 40 grams of fuming nitric acid is added over a period of 0.5 hour. The reaction mass is then stirred for a period of 6 minutes. Over a period of 10 minutes while maintaining the reaction mass at 20°-22° C., 10 grams of concentrated sulfuric acid is added to the reaction mass. The reaction mass is then heated to a temperature in the range of 26°-30° C. with stirring and maintained at that temperature for a period of four hours. At the end of the four hour period, the reaction mass is added to water and a solid is formed which precipitates out. The resulting crystals are washed with two 500 ml portions of water. The crystals melt at 99.5° C.

Figure 1:
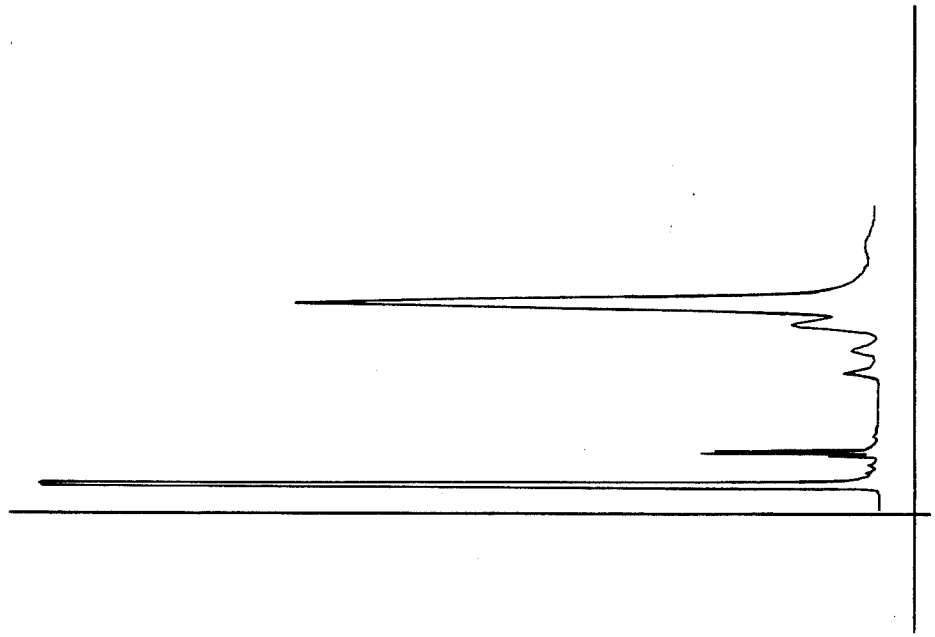
FIG. 1 is the GLC profile of the crude reaction product of Example I containing the compound having the structure.

FIG. 1 is the GLC profile for the crude reaction product.

FIG. 2 is the NMR spectrum for the compound having the structure:

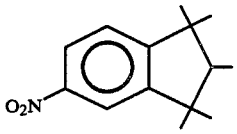

produced as indicated, supra.

The compound having the structure:

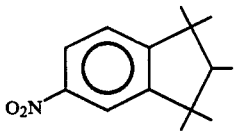

has an intense sweet, substantive, long-lasting, musky aroma having a strength and substantivity four times as great as any other nitro musk known in the prior art.

EXAMPLE II

PREPARATION OF 1,1,2,3,3,6-HEXAMETHYL-5-NITRO INDANE

Reaction:

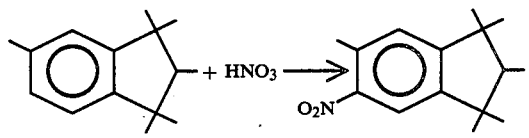

To a 500 ml reaction vessel equipped with stirrer, thermometer, reflux condensor, addition funnel and cooling bath is placed 51 grams of 1,1,2,3,3,6-hexamethyl indane having the structure:

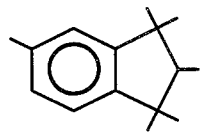

(51 grams) in admixture with 100 grams of acetic acid. The resulting mixture is cooled to 10° C. Over a period of 0.5 hours, 40 grams of fuming nitric acid is added to the reaction mass, while maintaining the reaction mass at 10° C. Over a period of 10 minutes, 10 grams of concentrated sulfuric acid is then added to the reaction mass. The reaction mass is then heated to 25° C. and maintained at 25° C. for a period of 3.5 hours. At the end of the 3.5 hour period, the reaction mass is quenched with ice water (500 ml) and crystals are formed. The crystals are then re-crystallized from water. The melting point of the resulting crystals is 115.7° C. NMR, IR and mass spectral anaylses yield the information that the compound has the structure:

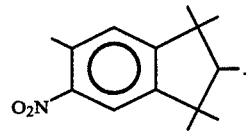

FIG. 3 is the GLC profile of the reaction product.

FIG. 4 is the NMR spectrum for the compound having the structure:

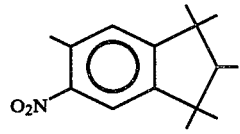

produced as indicated, supra.

The compound having the structure:

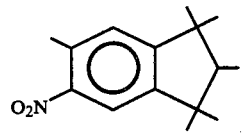

has a sweet, musky aroma which is intense, long-lasting and substantive and has an intensity and substantivity at least four times as great as any other nitro musks in the prior art.

EXAMPLE III

MUSK PERFUME

The following musk perfume formulation is prepared:

| Ingredients | Parts by Weight | |
| --- | --- | --- |
| | III(A) | III(B) |
| Hexadecanolide | 10.0 | 10.0 |
| 1,5,9-trimethylcyclo-dodecatriene-1,5,9 | 5.0 | 5.0 |
| 3-Cyclohexadecen-1-one | 12.0 | 12.0 |
| Tetradecanone | 8.0 | 8.0 |
| The compound having the structure: | 4.0 | 0.0 |

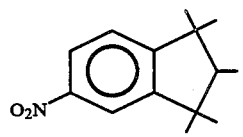

prepared according to Example I.

-continued

| Ingredients | Parts by Weight | |
|---|---|---|
| | III(A) | III(B) |
| The compound having the structure: 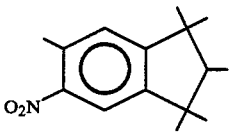 prepared according to Example II. | 0.0 | 4.0 |

The resulting perfume formulations in Examples III(A) and III(B) can both be described as "musky, animalic and leathery with intense, woody undertones".

EXAMPLE IV

PREPARATION OF COSMETIC POWDER COMPOSITIONS

Cosmetic powder compositions are prepared by mixing in a ball mill 100 grams of talcum powder with 0.25 grams of each of the substances set forth in Table I below. Each of the cosmetic powder compositions has an excellent aroma as described in Table I below:

TABLE I

| SUBSTANCE | AROMA DESCRIPTION |
|---|---|
| The compound having the structure: (O₂N- structure) prepared according to Example I. | A sweet, musky which is very intense, substantive and very long-lasting. |
| The compound having the structure: (O₂N- structure) prepared according to Example II. | A sweet musky aroma which is very intense, substantive and very long-lasting. |
| The perfume composition of Example III(A). | Musky animalic and leathery with intense, woody undertones. |
| The perfume composition of Example III(B). | Musky animalic and leathery with intense, woody undertones |

EXAMPLE V

PERFUMED LIQUID DETERGENTS

Concentrated liquid detergents (Lysine salt n-dodecylbenzene sulfonic acid as more specifically described in U.S. Pat. No. 3,948,818 issued on Apr. 6, 1976 incorporated by reference herein) with aroma nuances as set forth in Table I of Example IV, are prepared containing 0.10%, 0.15%, 0.20%, 0.25%, 0.30% and 0.35% of the substance set forth in Table I of Example IV. They are prepared by adding and homogeneously mixing the appropriate quantity of substance set forth in Table I of Example IV in the liquid detergent. The detergents all possess excellent aromas as set forth in Table I of Example IV, the intensity increasing with greater concentrations of substances as set forth in Table I of Example IV.

EXAMPLE VI

PREPARATION OF COLOGNES AND HANDKERCHIEF PERFUMES

Compositions as set forth in Table I of Example IV are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solution). Distinctive and definitive fragrances as set forth in Table I of Example IV are imparted to the colognes and to the handkerchief perfumes at all levels indicated.

EXAMPLE VII

PREPARATION OF SOAP CONCENTRATIONS

One hundred grams of soap chips [per sample] (IVORY ®, produced by the Proctor & Gamble Company of Cincinnati, Ohio), are each mixed with one gram samples of substances as set forth in Table I of Example IV until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I of Example IV.

EXAMPLE VIII

PREPARATION OF SOLID DETERGENT COMPOSITIONS

Detergents are prepared using the following ingredients according to Example I of Canadian Pat. No. 1,007,948 (incorporated by reference herein):

| Ingredient | Percent by Weight |
|---|---|
| "NEODOL ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example IV. Each of the detergent samples has an excellent aroma as indicated in Table I of Example IV.

EXAMPLE IX

Utilizing the procedure of Example I at column 15 of U.S. Pat. No. 3,632,396 (the disclosure of which is incorporated herein by reference), non-woven cloth substrates useful as drier-added fabric softening articles of manufacture are prepared wherein the substrate, the substrate coating, the outer coating and their perfuming material are as follows:
1. A water "dissolvable" paper ("Dissolvo Paper");
2. Adogen 448 (m.p. about 140° F.) as the substrate coating; and
3. An outer coating having the following formulation m.p. about 150° F.):
57% $C_{20-22}$ HAPS 22% isopropyl alcohol
20% anti-static agent
1% of one of the substances as set forth in Table I of Example IV.

Fabric softening compositions prepared according to Example I at column 15 of U.S. Pat. No. 3,632,396 having the aroma characteristics as set forth in Table I of Example IV, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example IV is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table I of Example IV, supra.

EXAMPLE X

HAIR SPRAY FORMULATIONS

The following hair spray formulation is prepared by first dissolving PVP/VA E-735 copolymer manufactured by the GAF Corporation of 140 West 51st Street, New York, N.Y., in 91.62 grams of 95% food grade ethanol. 8.0 Grams of the polymer is dissolved in the alcohol. The following ingredients are added to the PVP/VA alcoholic solution:

| Ingredient | Percent by Weight |
| --- | --- |
| Dioctyl sebacate | 0.05 |
| Benzyl alcohol | 0.10 |
| Dow Corning 473 fluid (prepared by the Dow Corning Corporation) | 0.10 |
| Tween 20 surfactant (prepared by ICI America Corporation) | 0.03 |
| One of the perfumery substances as set forth in Table I of Example IV, supra. | 0.10 |

The perfuming substances as set forth in Table I of Example IV add aroma characteristics as set forth in Table I of Example IV which are rather intense and aesthetically pleasing to the users of the soft-feel, good-hold pump hair sprays.

EXAMPLE XI

CONDITIONING SHAMPOOS

Monamid CMA (prepared by the Mona Industries Company) (3.0 weight percent) is melted with 2.0 weight percent coconut fatty acid (prepared by Proctor & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepen Chemical Company (35.0 weight percent). The resulting mixture is heated to 60° C. and mixed until a clear solution is obtained (at 60° C.). This material is "COMPOSITION A".

GAFQUAT ® 755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "COMPOSITION B".

The resulting "COMPOSITION A" & "COMPOSITION B" are then mixed in a 50:50 weight ratio of A:B and cooled to 45° C. and 0.3 weight percent of perfuming substance as set forth in Table I of Example IV is added to the mixture. The resulting mixture is cooled to 40° C. and blending is carried out for an additional one hour in each case. At the end of this blending period, the resulting material has a pleasant fragrance as indicated in Table I of Example IV.

What is claimed is:

1. The compound having the structure:

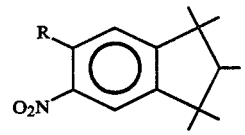

wherein R is hydrogen or methyl, or a mixture thereof.

2. A process for augmenting or enhancing the aroma of a perfume composition comprising the step of adding to said perfume composition at least one compound defined according to claim 1.

3. A process for augmenting or enhancing the aroma of a solid or liquid anionic, cationic, nonionic or zwitterionic detergent comprising the step of adding to said anionic, cationic, nonionic or zwitterionic detergent, an aroma augmenting or enhancing amount of a compound defined according to claim 1.

4. A process for augmenting or enhancing the aroma of a fabric softener composition or fabric softener article comprising the step of adding to said fabric softener composition or fabric softener article, an aroma augmenting or enhancing quantity of at least one compound defined according to claim 1.

5. A cologne composition comprising ethanol, water and at least one compound defined according to claim 1.

6. A cosmetic comprising a cosmetic base and intimately admixed therewith an aroma augmenting or enhancing quantity of at least one compound defined according to claim 1.

* * * * *